United States Patent [19]
Forzatti et al.

[11] Patent Number: 4,563,440
[45] Date of Patent: Jan. 7, 1986

[54] PROCESS FOR PREPARING AN OXIDATION CATALYST

[75] Inventors: Pio Forzatti, Monza; Ferruccio Trifiro, Bologna; Pierluigi Villa, Milan, all of Italy

[73] Assignee: Stamicarbon B.V., Licensing Subsidiary of DSM, Geleen, Netherlands

[21] Appl. No.: 577,756

[22] Filed: Feb. 7, 1984

[30] Foreign Application Priority Data

Feb. 8, 1983 [EP] European Pat. Off. ........ 83200198.6

[51] Int. Cl.$^4$ ..................... B01J 21/06; B01J 23/84; B01J 23/88
[52] U.S. Cl. .................................. 502/215; 502/309; 502/338
[58] Field of Search ...................... 502/215, 309, 338; 423/594; 568/477; 260/465.3

[56] References Cited

U.S. PATENT DOCUMENTS 3,546,138 12/1970 Callahan et al. ..................... 502/249
3,990,999 11/1976 Gasson et al. ........................ 502/309
4,380,664 4/1983 Ishii et al. ........................ 502/310 X

FOREIGN PATENT DOCUMENTS 1382733 2/1975 United Kingdom ............. 260/465.3

Primary Examiner—W. J. Shine
Attorney, Agent, or Firm—Cushman, Darby & Cushman

[57] ABSTRACT

This invention provides a catalyst composition suitable for the gas phase oxidation, ammoxidation and oxidative dehydrogenation of olefins to unsaturated aldehydes, unsaturated nitriles and dienes respectively. The catalyst composition comprises, as active catalyst component, a solid solution of Fe, Sb and Ti oxides which has a rutile type crystal structure which is present in the composition in an amount of at least 80 wt. %, and which is represented by the empirical formula $Fe_xSb_yTi_zO_w$, wherein, for $x=1$, y is in the range of 0.5 to 10, z is in the range of 0.16 to 209 and w represents the number of oxygen atoms corresponding to the oxides of the above elements. The catalyst component is prepared by co-precipitating metal oxides from solutions of corresponding metal salts followed by calcination at 600°–1000° C. of the washed and dried precipitate.

3 Claims, No Drawings

PROCESS FOR PREPARING AN OXIDATION CATALYST

FIELD OF THE INVENTION

This invention relates to catalyst compositions used in oxidation reactions and to processes for preparing them. The compositions are suitable for use in the gas phase oxidation of olefins to unsaturated aldehydes, in the gas phase ammoxidation of olefins to unsaturated nitriles, and in the gas phase oxidative dehydrogenation of olefins to dienes.

BACKGROUND OF THE INVENTION

Industrial developments over the last 20 years in the field of intermediates for producing plactics and synthetic fibers have led to studies of processes and catalysts for oxidizing olefins, and in particular for the oxidation of propylene to acrolein and acrylonitrile. In view of the large capacities of industrial plants where these types of oxidative reactions are carried out, it is strongly desired to obtain conversions as high as possible, either for economic reasons (even a slightly higher conversion can result in significantly increased profits) or for environmental reasons (reduced byproducts require less effort to eliminate and also reduce environmental pollution). A further important consideration relates to industrial catalysts' mechanical stability and ruggedness, particularly abrasion resistance which is an important consideration when using catalysts in fluidized beds.

Many oxidation and ammoxidation catalysts have been described in the patent literature. U.S. Pat. No. 2,904,580 discloses a catalyst composed mainly of bismuth phosphomolybdate. U.S. Pat. No. 3,198,750 discloses a catalyst composed mainly of oxides of Sb and U. Italian Pat. No. 682,880 discloses a catalyst comprising Ce, Mo and Te oxides. Additional oxidation and ammoxidation Fe and Sb oxide-based catalysts are known, such as those described in Japanese P No. 420,264, U.K. Pat. No. 983,755 and U.S. Pat. No. 3,197,419. It is also known that adding particular promoters to such catalysts provides improved yields in the ammoxidation of propylene as described, for example, in U.S. Pat. Nos. 3,338,952 and 3,546,138 wherein 30 different elements are presented as suitable promoters of Fe and Sb oxide-based catalysts when the amount of promoters is in the range of 1 to 10%. The catalysts can be used as such or supported on alumina, silica, titanium dioxide, zirconium dioxide, and the like. For example, U.K. Pat. No. 1,492,115 claims an Fe-Sb oxide-based catalyst which is promoted with other elements and which may be used either as such or supported, preferentially on silica.

However, these known catalysts have generally been found not to be entirely satisfactory with respect to one or more characteristics such as acrylonitrile yield, mechanical resistance when employed in fluidized beds, cost, procedure for preparing the catalyst, and stability with respect to long term catalytic activity and selectivity.

SUMMARY OF THE INVENTION

It has now been found possible to prepare an active catalyst component which has remarkable catalytic properties and good attrition resistance, and which retains its initial activity even after prolonged use. Advantageously, the catalyst may be prepared via a relatively facile process using inexpensive starting materials.

"Catalyst component" as used in the specification and claims refers to a solid solution which consists essentially of oxides Fe, Sb and Ti, as described hereinbelow, and which is itself catalytically active. A "catalyst composition" as used in the specification and claims may refer to the active catalyst component alone but, advantageously, the "catalyst composition" also includes one or more promoters.

DETAILED DISCUSSION

According to the present invention the active catalyst component consists of a solid solution having a rutile type crystal structure formed with Fe, Sb, and Ti oxides. A requirement of the invention, therefore, is that titanium oxide interact with Fe and Sb oxides in a manner which yields a solid solution, i.e. a single crystal phase.

The active catalyst component which satisfies this requirement consists essentially of a solid solution of Fe, Sb, and Ti oxides, said solid solution having a rutile type crystal structure represented by the empirical formula $$Fe_xSb_yTi_zO_w$$

wherein, for $x=1$, y is in the range of from 0.5 to 10, z is in the range of from 0.16 to 209, and w represents the number of oxygen atoms corresponding to the oxide of the catalyst component having the above empirical formula. The preferred value of $x/y$ is in the range of 0.2 to 1 and that of $z/(x+y+z)$ is in the range of from 0.2 to 0.9.

The active catalyst component according to the invention can be employed as such or in combination with at least one compound containing, as promoter, a metal selected from the group consisting of Mo, V, W, Bi and Te. Catalyst compositions containing the promoters must contain not less than 80 wt. % of the active catalyst component. The promoters, calculated as metal oxides, should be present in an amount of at least 0.2 wt. % based on the composition. The promoters are advantageously substantially dissolved in the solid phase of the active ingredient with no formation of separate crystal phases.

The catalyst composition displays remarkable activity and stability when used in the gas phase oxidation of propylene to acrolein, the ammoxidation of propylene to acrylonitrile, and in the oxidative dehydrogenation of olefins to dienes. In particular, the catalyst composition permits achieving the ammoxidation of propylene to acrylonitrile in very high yield and selectivity (these terms are hereinafter precisely defined, see the Examples) even when using low oxygen/propylene and ammonia/propylene ratios over relatively wide temperature ranges. The active catalyst component's (or composition's) hardness and resistance both to abrasion and to thermal shock permit it to be used as such, i.e. without need to be supported, even when operating in a fluidized bed.

The above combination of properties is not shown by Fe and Sb oxide-based catalysts when used either as such or in conjunction with Ti oxide employed as promoter and/or support. Also in the latter case it is impossible to obtain a single phase when using a preformed $TiO_2$ support, even if very high temperatures are employed to calcine the supported catalyst.

To prepare the active catalyst component it is important to provide intimate contact between the different constituents of the catalyst component before any calcination step is conducted. Calcining may then be used to effect a solid state reaction which yields a single crystal phase having a rutile type structure.

The present invention provides such intimate contact preferably by coprecipitating the constituents (i.e. the oxides of Fe, Sb and Ti) from aqueous solutions of their salts. Suitable soluble salts that can be used are, for iron, the nitrate, oxalate, chloride, or acetate salts; for antimony, the pentachloride salt or hydrolysis products thereof; for titanium, the tetrachloride, tetraethyltitanate or tetraisopropyltitanate and alkaline hydrolysis products thereof.

The coprecipitation of the above metal salts as oxides from the aqueous salt solution is performed by adding to the solution volatile bases such as ammonia, aliphatic amines of low molecular weight such as methylamine, ethylamine, or propylamine, heterocyclic compounds such as pyridine, quinoline and the like, or aqueous solutions of these bases. The temperature of coprecipitation may be in the range of from room temperature to the boiling point of the solution; however it is preferred to work at temperatures in the range of from 20° to 50° C. because of the fact that the bases are volatile. The pH of the solution changes during coprecipitation within the range of below 2 up to about 9. The coprecipitation may, in any case, be considered complete when the pH permanently stabilizes or levels out at a value of about 8.

A particularly advantageous preparation procedure for coprecipitating the mixture of oxides consists essentially in adding a solution of antimony chloride and titanium tetrachloride to an aqueous solution of iron chloride. Once the solutions have been combined, the coprecipitation of the Fe, Sb, and Ti as oxides is effected by adding an aqueous solution of from 15% to 30% ammonia to adjust the final pH value to 8 while maintaining the temperature in the range of from 15° to 50° C. The precipitate is separated from the solution and washed with (preferably hot) water, following which it is dried at 110°–130° C. A preferred drying procedure can be performed by spray drying with warm air. The dried product is then calcined at high temperature to form the finished active catalyst component.

The precipitation of each metal is substantially complete. Assuming complete precipitation, the amount (e.g., in moles) of each metal added to solution initially as the salt can therefore be calculated depending on the values of x, y, and z ultimately desired in the empirical formula $Fe_xSb_yTi_zO_w$.

The calcining conditions (i.e. temperature and time) are very important because they determine the crystalline transformation of the oxides (i.e. to single phase) and, therefore, for the activity and the other properties of the active catalyst component of the catalyst composition of this invention. Although the optimum calcination conditions can vary depending on the desired composition of the catalyst component, it is required in all cases to effect calcination at a temperature between 600° C. and 1000° C. Below 600° C. transformation of the oxides to a single crystalline phase is not effected, while temperatures higher than 1000° C. are not advisable because the morphology of the active ingredient may vary and consequently reduce catalytic activity or selectivity.

In a preferred form of the present invention the calcination is carried out as a two step procedure, the first step being a pretreatment (e.g. to remove volatile substances such as amines) which is carried out by heating the precipitate for a period of time of from 2 to 24 hours at a temperature between 200° and 600° C. The second step consists essentially in actually calcining by further heating the product from the first step in a range of from 600° to 900° C. for a period of time between 1 and 48 hours.

If the active catalyst component obtained as described above is combined with one or more promoting substances, the point at which the promoters are added while the catalyst component is being made is not critical. That is, it is possible to add one or more desired promoters to the active catalyst component after it has been calcined, to the precipitate before calcination is carried out, or at any other point in the procedure which is considered convenient.

In a preferred form of the invention, however, the active component is calcined, and then impregnated with a solution, in a suitable solvent, of one or more promoter salts which are soluble and which decompose to form oxides at high temperature. Then the drying cycle (used to dry the precipitate) and the first (i.e. pretreatment) step of the preferred calcination procedure previously described are repeated. It is not necessary to repeat the high temperature second calcination step. i.e. above 600° C.

Soluble and decomposable promoter salts for the impregnation of the calcined active ingredient which are preferred are ammonium paramolybdate, ammonium paratungstate, ammonium metavanadate, bismuth nitrate and telluric acid. The same salts are also suitable as promoters for mixing with the precipitate if it is desired to form the composition at an earlier stage during preparation of the active catalyst component.

In order to further illustrate and explain the present invention, the following examples are provided which describe the preparation and use of the active catalyst component and catalyst compositions.

EXAMPLE 1

50 ml of anhydrous $SbCl_5$ were dissolved in 150 ml of anhydrous $TiCl_4$. The resulting solution was added dropwise and with stirring to a solution consisting of 53.11 gm of $FeCl_3.6H_2O$ and 6.52 liters of deionized water. The water volume was such that the final concentration of Fe+Sb+Ti was approximately 0.3M. Then, 1100 ml of 15% aqueous ammonia were added dropwise to reach a final pH value of 8.

A suspended precipitate resulted which was allowed to settle for 2 hours, during which time the supernatant liquid was slowly decanted. The precipitate was then filtered and washed by being added to 3.9 liters of hot deionized water and maintained at the boiling point for 5 minutes. The volume of water was such that the concentration of Fe+Sb+Ti was approximately 0.5M. The suspension was then filtered and the wash procedure was repeated. After this the precipitate was dried at 120° C., for 24 hours, pretreated in a first step by heating at 350° C. for 15 hours, ground to 35–52 mesh and then calcined in a second step at 900° C. for 1.5 hours. This calcined product represented the active catalyst component. Its X-ray diffraction pattern corresponds to that of compounds No. 9 in Table 1. The product was determined to have empirical formula $FeSb_2Ti_{6.98}O_{19.98}$.

EXAMPLE 2

A catalyst component was prepared as in Example 1, except that the second step of the calcination was performed at 700° C. for 3 hours. Then 0.3699 gm of $(NH_4)_6Mo_7O_{24}.4H_2O$ and 0.9622 gm of $H_6TeO_6$ were dissolved in separate volumes of deionized water. The two solutions were mixed and the volume of the resulting solution brought to 6.8 ml by adding water. This solution was used to impregnate, in a rotary evaporator, 20 gm of the catalyst component. The catalyst component so-impregnated was dried at 125° C. for 15 hours and calcined by increasing the temperature (heating rate=25° C./30 min) up to 500° C., which temperature was maintained for 15 hours. The resulting material represented a catalyst composition. The X-ray diffraction patterns are very similar to those of component No. 9 in Table 1. The product had the basic empirical formula $FeSb_2Ti_{6.98}O_{19.98}$ modified due to the addition of 0.956% and 2.541% by weight of Mo and Te.

EXAMPLES 3-6

Catalyst compositions corresponding to Examples 3-6 were prepared by the method of Example 2, except that the second step calcination temperature and time were varied as noted in Table 2, below. Table 2 gives some data and preparation conditions pertaining to the catalyst compositions of these examples, as well as to the catalyst component of Example 1.

EXAMPLE 7-12

Active catalyst components having different Ti contents were prepared according to the procedure outlined in example 1. The catalyst components are designated, respectively as components No. 7, No. 8, No. 9, No. 10, No. 11, and No. 12 in Table 1, wherein each component No. corresponds to the same Example number. The amount of Ti is specified in terms of the ratio $z/(x+y+z)$ where x, y, z are numbers which refer to the aforementioned empirical formula.

Table 1, below, presents the characteristic d values of the X-ray diffraction spectra for each of component Nos. 7-12. For comparison, Table 1 also presents the X-ray diffraction patterns of rutile $TiO_2$ (designated as component No. X).

By increasing the Fe and Sb content with respect to the Ti content, a continuous shift of the X-ray (2) values is evident, which results in higher corresponding d values, thus indicating the formation of a solid solution. Calculations performed according to standard methods of unit cell parameters do in fact confirm that the oxides of Fe and Sb are dissolved into $TiO_2$ forming a solid solution having a rutile type structure.

EXAMPLE 13

The catalyst component described in Example 1, ground to 35-52 mesh, was charged into an electrically heated reactor (i.d.=5.5 mm). The following gas composition (in % by volume) was fed to the reactor: $C_3H_6$, 6%; $O_2$, 13%; $N_2$, 81%. The reaction temperature was varied within the range of from 322° to 472° C.; a gas hourly space velocity (GHSV) of 2700 $h^{-1}$ was employed and the pressure was set at 1.35 atmospheres.

The results are reported below.

TABLE
Example 13

| Temperature | Conversion[1] | Selectivity[2] | Yield[3] |
|---|---|---|---|
| 322° C. | 1.5 | 100 | 1.5 |
| 352° C. | 6. | 90 | 5.4 |
| 382° C. | 8. | 80 | 6.4 |
| 412° C. | 13. | 75 | 9.7 |
| 442° C. | 18. | 71 | 12.8 |
| 472° C. | 24. | 64 | 15.4 |

[1]% conversion of propylene: (moles of propylene reacted/moles of propylene fed) × 100
[2]% selectivity to acrolein: (moles of acrolein formed/moles of propylene reacted) × 100
[3]% yield of acrolein: (moles of acrolein formed/moles of propylene fed) × 100.

Basically, only carbon oxides were detected as reaction by-products.

EXAMPLES 14-18

The catalyst compositions described in Examples 2, 3, 4, 5 and 6, ground to 35-52 mesh, were charged to a reactor as described in example 13. A gaseous reaction mixture having the following volumetric composition was fed to the reactor: $C_3H_6$, 6%; $O_2$, 13%; $NH_3$, 7%; $N_2$, 74%. Other experimental conditions were: pressure, 1.5 atm; reaction temperature, variable; GHSV, slightly different depending on the catalyst. Acrylonitrile was the main product; acetonitrile, carbon oxides, HCN and acrolein were found as the main byproducts. The results, given in terms of % propylene conversion, % acrylonitrile selectivity and % acrylonitrile yield, calculated as in Example 13, are presented below. Each Catalyst No. refers to the corresponding Example describing how it was made.

TABLE
Example 14
Catalyst No. 2 (GHSV = 520 $h^{-1}$)

| Temperature | Conversion[4] | Selectivity[5] | Yield[6] |
|---|---|---|---|
| 390° C. | 73 | 76 | 56 |
| 420° C. | 92 | 82 | 75 |
| 450° C. | 99 | 90 | 79 |

[4]% conversion of propylene: (moles of propylene reacted/moles of propylene fed) × 100
[5]% selectivity to acrylonitrile: (moles of acrylonitrile formed/moles of propylene reacted) × 100
[6]% yield of acrylonitrile: (moles of acrylonitrile formed/moles of propylene fed) × 100

TABLE
Example 15
Catalyst No. 3 (GHSV = 520 $h^{-1}$)

| Temperature | Conversion[4] | Selectivity[5] | Yield[6] |
|---|---|---|---|
| 400° C. | 50 | 92 | 46 |
| 420° C. | 70 | 73 | 51 |
| 450° C. | 74 | 55 | 41 |

(4)-(6), See Table-Example 14.

TABLE
Example 16
Catalyst No. 4 (GHSV = 510 $h^{-1}$)

| Temperature | Conversion[4] | Selectivity[5] | Yield[6] |
|---|---|---|---|
| 390° C. | 69 | 81 | 56 |
| 430° C. | 98 | 82 | 80 |
| 450° C. | 99 | 81 | 80 |

(4)-(6), See Table-Example 14.

TABLE

Example 17
Catalyst No. 5 (GHSV = 510 h$^{-1}$)

| Temperature | Conversion[4] | Selectivity[5] | Yield[6] |
|---|---|---|---|
| 390° C. | 69 | 81 | 56 |
| 430° C. | 98 | 89 | 87 |
| 450° C. | 99 | 85 | 84 |

(4)–(6), See Table-Example 14.

TABLE

Example 18
Catalyst No. 6 (GHSV = 640 h$^{-1}$)

| Temperature | Conversion[4] | Selectivity[5] | Yield[5] |
|---|---|---|---|
| 390° C. | 71 | 74 | 53 |
| 420° C. | 98 | 82 | 80 |
| 450° C. | 99 | 79 | 78 |

(4)–(6), See Table-Example 14.

Catalyst Nos. 2–6 shows excellent stability with use, no indication of either mechanical degradation or activity decay being detected after 200 hours time on stream.

TABLE 1

X-ray diffraction data for Catalyst Components of Examples 7–12, plus data for TiO$_2$ Fe$_x$Sb$_y$Ti$_z$O$_w$ x/y=0.5

| TiO$_2$ component No. X | | z/(x+y+z)=0.905 component No. 7 | | z/(x+y+z)=0.85 component No. 8 | | z/(x+y+z)=0.7 component No. 9 | | z/(x+y+z)=0.5 component No. 10 | | z/(x+y+z)=0.25 component No. 11 | | z/(x+y+z)=0.1 component No. 12 | |
|---|---|---|---|---|---|---|---|---|---|---|---|---|---|
| d(Å) (1) | I/I$_o$ (2) | d(Å) (1) | I/I$_o$ (2) | d(Å) (1) | I/I$_o$ (2) | d(Å) (1) | I/I$_o$ (2) | d(Å) (1) | I/I$_o$ (2) | d(Å) (1) | I/I$_o$ (2) | d(Å) (1) | I/I$_o$ (2) |
| 3.253 | 100 | 3.248 | 100 | 3.255 | 100 | 3.255 | 100 | 3.267 | 100 | 3.263 | 100 | 3.276 | 100 |
| 2.492 | 39 | 2.494 | 53 | 2.498 | 44 | 2.509 | 61 | 2.528 | 48 | 2.537 | 52 | 2.555 | 58 |
| 2.302 | 8 | 2.298 | 8 | 2.301 | 8 | 2.303 | 18 | 2.312 | 12 | 2.309 | 13 | 2.317 | 16 |
| 2.189 | 18 | 2.190 | 21 | 2.193 | 18 | 2.202 | 20 | 2.216 | 10 | 2.223 | 7 | 2.237 | 6 |
| 2.055 | 7 | 2.053 | 8 | 2.056 | 10 | 2.059 | 12 | 2.067 | 3 | 2.062 | 5 | 2.072 | 4 |
| 1.688 | 49 | 1.689 | 62 | 1.691 | 57 | 1.697 | 58 | 1.705 | 48 | 1.708 | 46 | 1.716 | 52 |
| 1.624 | 15 | 1.624 | 20 | 1.625 | 17 | 1.629 | 20 | 1.634 | 14 | 1.633 | 13 | 1.638 | 15 |
| 1.480 | 7 | 1.487 | 10 | 1.486 | 6 | 1.498 | 21 | 1.508 | 5 | 1.522 | 5 | 1.532 | 7 |
| 1.453 | 5 | 1.453 | 10 | 1.454 | 7 | 1.457 | 16 | 1.461 | 10 | 1.462 | 11 | 1.462 | 12 |

(1) d represents the interplane spacing (in Angstroms)
(2) I/I$_o$ represents the % ratio between the intensity of the X-ray lines, the most intense X-ray line being taken as 100.

TABLE 2

Examples 1–6

| Example No. | empirical formula | conditions for step second calcination | z/(x + y + z) | elements added as promoters (wt. %) |
|---|---|---|---|---|
| 1 | FeSb$_2$Ti$_{6.98}$O$_{19.98}$ | 900° C., 1.5 hr | 0.7 | — |
| 2 | FeSb$_2$Ti$_{6.98}$O$_{19.98}$ | 700° C., 3 hr | 0.7 | Mo, 0.956%; Te, 2.541% |
| 3 | FeSb$_2$Ti$_{6.98}$O$_{19.98}$ | 900° C., 1,5 hr | 0.7 | Mo, 0.956%; Te, 2.541% |
| 4 | FeSb$_2$Ti$_{4.5}$O$_{26.4}$ | 700° C., 3 hr | 0.6 | Mo, 1.193%; Te, 3.172% |
| 5 | FeSb$_{2.5}$Ti$_{4.5}$O$_{26.4}$ | 700° C., 3 hr | 0.56 | Mo, 1.069%; Te, 2.844% |
| 6 | FeSb$_2$Ti$_{1.286}$O$_{8.57}$ | 700° C., 3 hr | 0.3 | Mo, 1.752%; Te, 4.66% |

What is claimed is:

1. A process for preparing a catalytic composition comprising, as active catalyst component, a solid solution consisting essentially of Fe, Sb, and Ti oxides, said catalyst component having a rutile type crystal structure and the empirical formula Fe$_x$Sb$_y$Ti$_z$O$_w$ wherein, for x=1, y is between 0.5 and 10, z is between 0.16 and 209, and w represents the number of oxygen atoms corresponding to the oxide of said catalyst component having said empirical formula, said process consisting essentially in the combination of steps of:
dissolving soluble salts of Fe, Sb, and Ti in an aqueous medium;
adjusting the pH of said medium to about 8 by adding, at a temperature between 15° and 50° C., ammonia or a nitrogen-containing organic base thereto, whereby a precipitate forms;
filtering and washing said precipitate and then drying at 110°–130° C.; and thereafter
calcining said precipitate to produce said catalyst component by:
(i) first pretreating said dried precipitate by heating at a temperature between 200° and 600° C. for 2 to 24 hours; and
(ii) heating the product from (i) at a temperature of between 600° and 900° C. for 1 to 48 hours.

2. The process of claim 1, further comprising the steps of:
impregnating said calcined catalyst component with a solution of at least one soluble compound containing, as promoter, an element selected from the group consisting of Mo, V, W, Bi and Te;
drying the thus impregnated component at a temperature of 110°–130° C.; and
calcining the dried component at a temperature between 200°–600° C. for 2 to 24 hours.

3. The process of claim 2 wherein said soluble compound is selected from the group consisting of ammonium paramolybdate, ammonium paratungstate, ammonium metavanadate, bismuth nitrate, and telluric acid, and wherein said promoter containing solution is aqueous.

* * * * *